United States Patent
Filippi et al.

(10) Patent No.: US 9,914,691 B2
(45) Date of Patent: Mar. 13, 2018

(54) (3R) EPIMER OF OCTAHYDRO-7,7-DIMETHYL-8-METHYLENE 1H-3A, 6-METHANOAZULENE-3-YL ACETATE, COMPOSITION, SYNTHESIS PROCESS AND USE OF SAID EPIMER

(71) Applicants: ROBERTET SA, Grasse (FR); UNIVERSITE DE NICE SOPHIA ANTIPOLIS, Nice (FR); CENTRE NATIONAL DE LA RECHERCHE SCIENTIFIQUE (CNRS), Paris (FR)

(72) Inventors: Jean-Jacques Filippi, Nice (FR); Emilie Belhassen, Saint-Laurent-du-Var (FR); Nicolas Baldovini, Nice (FR); Hugues Brevard, Grasse (FR)

(73) Assignees: ROBERTET SA, Grasse (FR); UNIVERSITE DE NICE SOPHIA ANTIPOLIS, Nice (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days.

(21) Appl. No.: 14/902,676

(22) PCT Filed: Jun. 25, 2014

(86) PCT No.: PCT/FR2014/051607
§ 371 (c)(1),
(2) Date: Jun. 8, 2016

(87) PCT Pub. No.: WO2015/001227
PCT Pub. Date: Jan. 8, 2015

(65) Prior Publication Data
US 2016/0280630 A1    Sep. 29, 2016

(30) Foreign Application Priority Data

Jul. 3, 2013 (FR) .................... 13 56482

(51) Int. Cl.
C07C 67/02 (2006.01)
C07C 69/145 (2006.01)
C11B 9/00 (2006.01)
C07C 67/40 (2006.01)

(52) U.S. Cl.
CPC ............ *C07C 69/145* (2013.01); *C07C 67/40* (2013.01); *C11B 9/0042* (2013.01); *C07B 2200/07* (2013.01); *C07C 2603/66* (2017.05)

(58) Field of Classification Search
None
See application file for complete search history.

(56) References Cited

FOREIGN PATENT DOCUMENTS

GB    1414704    * 11/1975

OTHER PUBLICATIONS

Kazutos et al., Agric. Biol. Chem., 53 (5), 1449-1450, 1989.*
March's Advanced Organic Chemistry (5th Ed. 2001), 151-155.*
Real World Drug Discovery, Rydzewski (2008), 42-43.*

* cited by examiner

*Primary Examiner* — Sudhakar Katakam
*Assistant Examiner* — Ana Z Muresan
(74) *Attorney, Agent, or Firm* — Browdy and Neimark, PLLC

(57) ABSTRACT

The first subject matter of the invention is the (3R) epimer of octahydro-7,7-dimethyl-8-methylene-1H-3a,6-methanoazulen-3-yl acetate [(octahydro-7,7-dimethyl-8-methylene-[3R,3aR,6R,8aR]-1H-3a,6-methanoazulen-3-yl acetate) or (R)-norzizaenylacetate] of formula I (I). The subject matter of the invention is also compositions comprising (R)norzizaenyl acetate and also a novel synthesis process and the use of said ester.

19 Claims, 1 Drawing Sheet

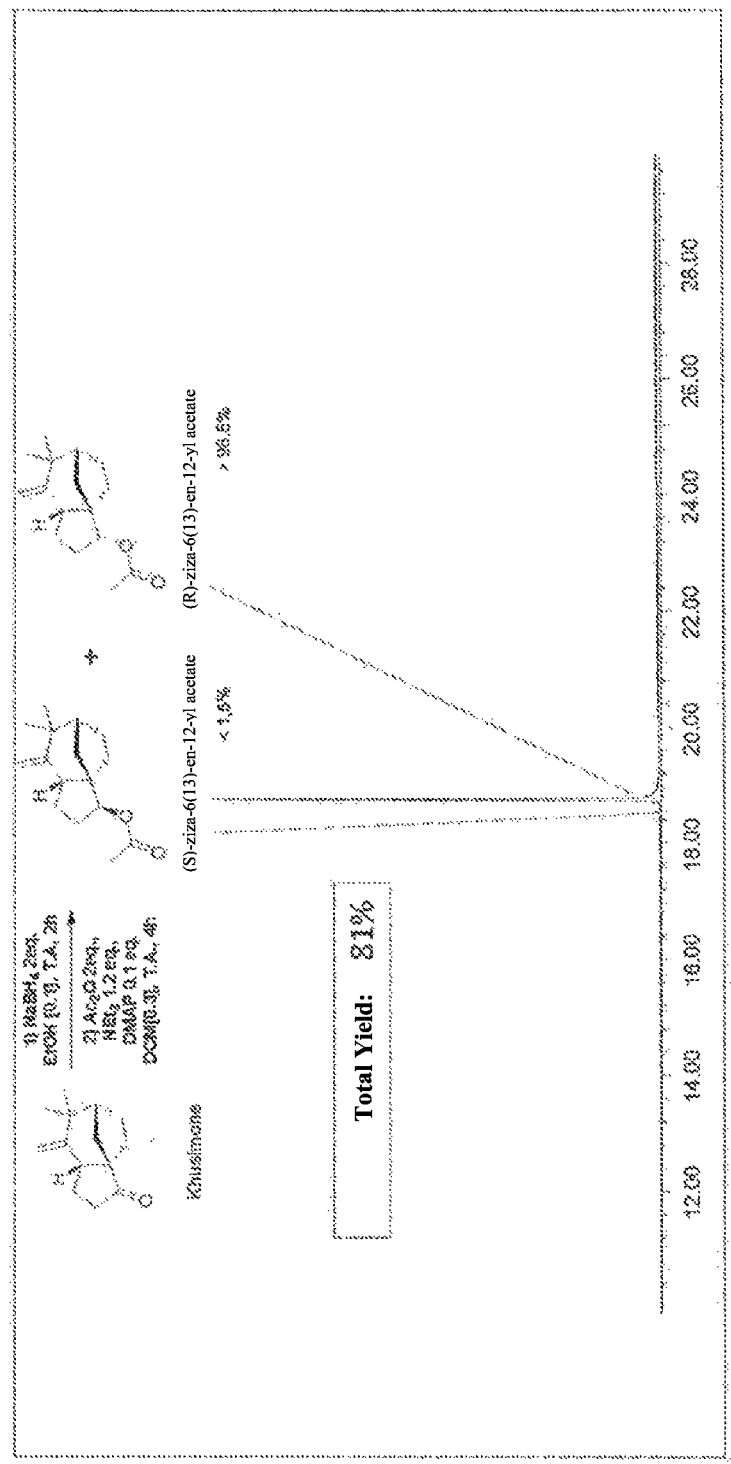

(3R) EPIMER OF OCTAHYDRO-7,7-DIMETHYL-8-METHYLENE 1H-3A, 6-METHANOAZULENE-3-YL ACETATE, COMPOSITION, SYNTHESIS PROCESS AND USE OF SAID EPIMER

The invention relates primarily to the (3R)-epimer of octahydro-7,7-dimethyl-8-methylene-1H-3a,6-methanoazulene-3-yl acetate (octahydro-7,7-dimethyl-8-methylene-[3R,3aR,6R,8aR]-1H-3a,6-methanoazulene-3-yl acetate) with formula I

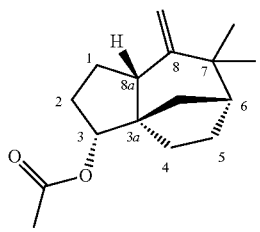

I also referred to herein as (2R)-12-norziza-6(13)-en-2-yl acetate.

The invention also relates to compositions with (2R)-12-norziza-6(13)-en-2-yl acetate, as well as a new synthesis method and use of said ester.

The term "Vetiver" designates in French the plants of the Poaceae (grasses) family. They consist of several species of the *Chrysopogon* (formerly *Vetiveria*) genus. A dozen species growing in tropical areas are known. The best known species is *Chrysopogon zizanioides*, which grows primarily in the Indian subcontinent. Two other species are frequently grown: *Chrysopogon nigritanus* in Southern Africa and *Chrysopogon nemoralis* in Southeast Asia.

The plant grows as large green tufts, and has roots, which grow vertically, that can reach depths of up to three meters (10 ft).

After distillation, the Vetiver roots produce a highly viscous essential oil used in perfumery. Vetiver essential oil belongs to the woody olfactory family. Vetiver essence is a fine and complex fragrance: woody, aromatic, green, earthy, sometimes slightly smoky or citrus-like.

Many fragrances on the market contain Vetiver essential oil, or derivatives thereof, as the key aromatic ingredient Studies conducted by the applicant on different Vetiver extracts, components, and derivatives have identified a number of main compounds that have an aromatic impact. Among these molecules affecting aroma, those having a zizaane backbone occupy a special place, including khusimone, whose structure corresponds to the formula II below

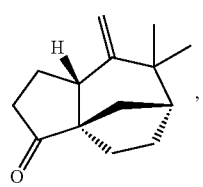

II which is known as the main aromatic ingredient in Vetiver. This substance has a woody odor, typical of Vetiver and reminiscent of the smell of Vetiver oil.

Vetiver essential oil of contains multiple components as shown by Weyerstahl's publications (see, for example, P. Weyerstahl et al., *Flavour and Fragrance Journal*, 2000, 15, 395-412). There are, in particular, ketones and alcohols. But Vetiver oil naturally contains very little or no acetate.

Analytical work completed by the applicant has outlined the essential contribution of (2R)-12-norziza-6(13)-en-2-yl acetate with formula I

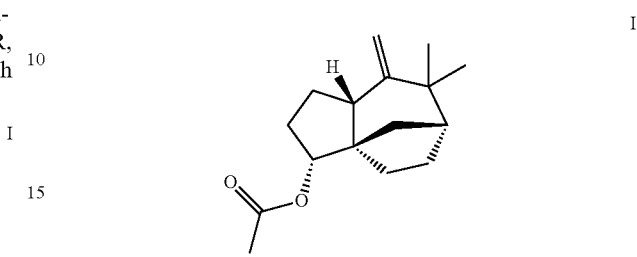

I that is a compound that has an important aromatic impact, with a woody note typical of Vetiver, very similar to that of khusimone. In the same work, it was possible to determine that its (3S)-epimer had a much lower aromatic profile.

At present, no synthetic aromatic material corresponding to (2R)-12-norziza-6(13)-en-2-yl acetate is commercially available. The lack of a synthetic substitute is partly due to the complex nature of sesquiterpenes, which comprise the essence of Vetiver and its derivatives.

In the prior art, reference CAS: 52771-08-1, called octahydro-7,7-dimethyl-8-methylene-1H-3a,6-methanoazulene-3-yl acetate, is mentioned without any further clarification as to the isomeric form of this compound (FR 2201841).

Likewise, the (3S)-epimer of octahydro-7,7-dimethyl-8-methylene-1H-3a,6-methanoazulene-3-yl acetate (octahydro-7,7-dimethyl-8-methylene-[3S,3aR,6R,8aR]-1H-3a,6-methanoazulene-3-yl acetate), otherwise referred to herein as (2S)-12-norziza-6(13)-en-2-yl acetate, is known (CAS No. 124601-88-3) (Sakurai, K. et al., *Agricultural and Biological Chemistry*, vol. 53, no. 5, pages 1449-1450 (1989)).

However, the (3R)-epimer of octahydro-7,7-dimethyl-8-methylene-1H-3a,6-methanoazulene-3-yl acetate [octahydro-7,7-dimethyl-8-methylene-[3S,3aR,6R,8aR]-1H-3a,6-methanoazulene-3-yl acetate, or (2R)-12-norziza-6(13)-en-2-yl acetate], has never been isolated or synthesized, especially in pure or substantially pure isomeric form, that is, more than 95% of the (R)-isomer.

After extensive research, the applicant has now developed a new 2-step synthesis method for (2R)-12-norziza-6(13)-en-2-yl acetate from khusimone.

Thus, the invention relates primarily to the (3R)-epimer of octahydro-7,7-dimethyl-8-methylene-1H-3a,6-methanoazulene-3-yl acetate [octahydro-7,7-dimethyl-8-methylene-[3R,3aR,6R,8aR]-1H-3a,6-methanoazulene-3-yl acetate or (2R)-12-norziza-6(13)-en-2-yl acetate], with formula I

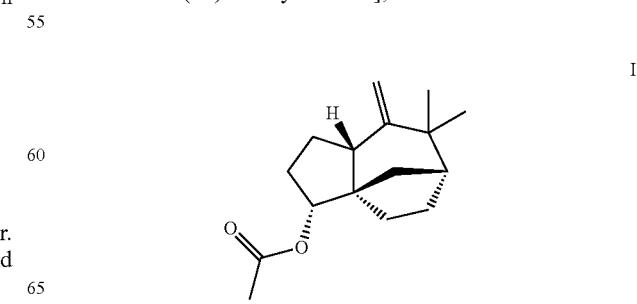

I

In one embodiment of the invention said compound is isolated.

By isolated it is understood that the solution containing said compound with formula I has undergone at least one purification step of such compound.

The invention also relates to a composition with at least (2R)-12-norziza-6(13)-en-2-yl acetate.

In a first embodiment of the invention the composition can only comprise the (R) form of 12-norziza-6(13)-en-2-yl acetate [(2R)-12-norziza-6(13)-en-2-yl acetate] and therefore does not comprise the (2S)-12-norziza-6(13)-en-2-yl acetate form, regardless of the amount of 12-norziza-6(13)-en-2-yl acetate in the composition.

In another embodiment of the invention the composition can comprise (2R)-12-norziza-6(13)-en-2-yl acetate and (2S)-12-norziza-6(13)-en-2-yl acetate in a weight ratio of the (2R)-12-norziza-6(13)-en-2-yl acetate form to the (2S)-12-norziza-6(13)-en-2-yl acetate form, [(R)/(S)], greater than 1.2, preferably greater than 1.5, regardless of the total amount of 12-norziza-6(13)-en-2-yl acetate in the composition.

The invention also relates to a new synthesis method of (2R)-12-norziza-6(13)-en-2-yl acetate (Formula I) by khusimone reduction (Formula II) in the presence of an organic solvent, followed by acetylation of the resulting alcohol (12-norziza-6(13)-en-2β-ol, Formula III) in the presence of a base, a nucleophilic catalyst and an aprotic solvent, according to the following reaction sequence.

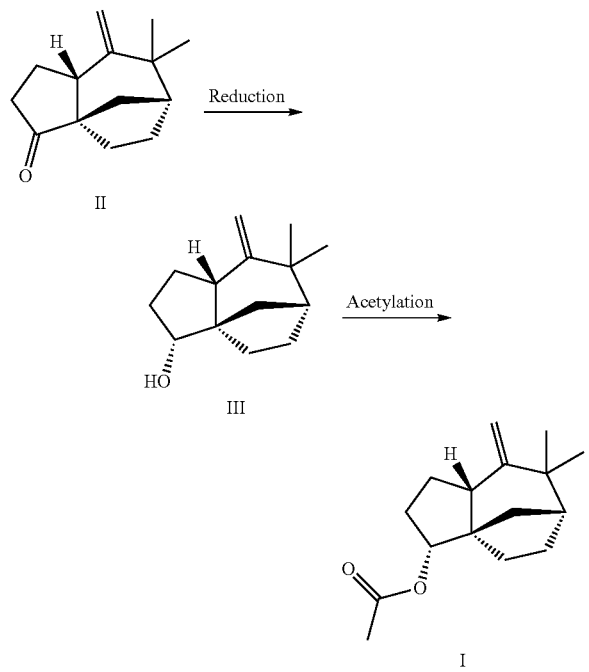

The new synthesis method proposed herein has the advantage, besides its simplicity, its relatively low cost and the possibility of industrialization, of eventually allowing the synthesis of (2R)-12-norziza-6(13)-en-2-yl acetate in a pure or nearly pure form. By pure or nearly pure, it is understood herein that at the end of the reaction, the reaction medium contains very little or virtually no (S)-epimer [(2S)-12-norziza-6(13)-en-2-yl acetate].

In fact, experience shows that it is possible to obtain, in two steps, up to 95% or even 98.5% of the (R)-form of 12-norziza-6(13)-en-2-yl acetate in the reaction medium (see Example 1).

Therefore, the invention relates to a synthesis method of (2R)-12-norziza-6(13)-en-2-yl acetate, comprised of a first step, the reduction of khusimone in the presence of a reducing agent and an organic solvent, and a second step, the acetylation of the product obtained in the first step in the presence of an organic solvent.

More specifically, in the first step of the method, according to the invention, the reduction reaction of khusimone can be carried out in the presence of a reducing agent which can be selected from lithium aluminum hydride (LiAlH$_4$), DiBAH (diisobutylaluminium hydride), sodium borohydride (NaBH$_4$), lithium borohydride (NaLiH$_4$) or potassium borohydride (KBH$_4$). Preferably, according to the invention, NaBH$_4$ can be used.

According to the invention, the reduction reaction of khusimone can be carried out with a molar ratio [(AR)/(K)] between the reducing agent (RA) and the khusimone (K) that can be between 0.5 and 5, preferably between 1 and 3, more preferably equal to 2.

According to the invention, the reduction reaction of khusimone can be carried out in the presence of an organic solvent which can be selected from methanol (MeOH), ethanol (EtOH), propanol, isopropanol, n-butanol, sec-butanol, isobutanol, t-butanol, tetrahydrofuran (THF), 1,4-dioxane, dimethylsulfoxide (DMSO), acetonitrile, or mixtures in all proportions of these solvents, for example, DMSO/MeOH, THF/MeOH, DMSO/THF, DMSO/dioxane mixtures. Preferably, according to the invention, the organic solvent can be ethanol.

According to the invention, the reduction of khusimone can be carried out at a temperature between −25° C. and the solvent reflux temperature. Preferably, the reaction can be started at a temperature between −25° C. and 25° C. (13° F. to 77° F.), more preferably −25° C. and 0° C. (13° F. to 32° F.). The reaction can then progress freely until it reaches solvent reflux temperature; it can then be kept at a temperature between 25° C. (77° F.) and the reflux temperature, until all reactants are exhausted. Most preferably, once the solvent reflux temperature has been reached, the reaction can be kept at this temperature.

Those of ordinary skill in the art will readily stop the reaction when it can be observed, by sample collection and analysis, that the reaction has reached the desired stage, for example, by measuring the removal of khusimone with gas chromatography or thin layer chromatography, or nuclear magnetic resonance.

According to the invention, the 12-norziza-6(13)-en-2β-ol (formula III) obtained in the first step can be directly converted into (2R)-12-norziza-6(13)-en-2-yl acetate (formula I) by acetylation by reacting said 12-norziza-6(13)-en-2β-ol with an acetylating agent (Ac) that can be selected from acetic anhydride, acetic acid, or acetyl chloride, in the presence of a base and a nucleophilic catalyst in an aprotic solvent.

According to the invention, the acetylation reaction of 12-norziza-6(13)-en-2β-ol can be carried out with a molar ratio [(Ac)/(Z)] between the acetylating agent (Ac) and 12-norziza-6(13)-en-2β-ol (Z) that can be between 1 and 5, preferably equal to 1.5.

According to the invention, the acetylation reaction of 12-norziza-6(13)-en-2β-ol can be carried out in the presence of an organic base that can be selected from N,N-diisopropylethylamine (DIPEA), triethylamine (Et$_3$N) or pyridine. Preferably, the acetylation reaction of 12-norziza-6(13)-en-2β-ol can be carried out in the presence of triethylamine.

According to the invention, the acetylation reaction of 12-norziza-6(13)-en-2β-ol can be carried out with a molar ratio [(OB)/(Z)] between the organic base (OB) and the 12-norziza-6(13)-en-2β-ol (Z) that can be between 0.1 and 5, preferably equal to 1.5.

According to the invention, the acetylation reaction of 12-norziza-6(13)-en-2β-ol can be carried out in the presence of an organic base that can be selected from 4-(N,N-dimethylamino)pyridine (DMAP), 1,4-diazabicyclo[2.2.2]octane (DABCO), 1,8-diazabicyclo[5.4.0]undec-7-ene (DBU) or N,N'-dicyclohexylcarbodiimide (DCC). Preferably, according to the invention, DMAP can be used.

According to the invention, the acetylation reaction of 12-norziza-6(13)-en-2β-ol can be carried out with a molar ratio [(NC)/(Z)] between the nucleophilic catalyst (NC) and the 12-norziza-6(13)-en-2β-ol (Z) that can be between 0.01 and 10, preferably equal to 0.1.

According to the invention, the acetylation reaction of 12-norziza-6(13)-en-2β-ol can be carried out in the presence of an aprotic solvent that can be selected from n-hexane, cyclohexane, 1,4-dioxane, dichloromethane (DCM), carbon tetrachloride ($CCl_4$), benzene, trichloroethylene ($Cl_2C=CHCl$), tetrachloro ($Cl_2C=CCl_2$), toluene, carbon disulfide ($CS_2$), diethyl ether ($Et_2O$), chloroform ($CHCl_3$), bromobenzene (PhBr), chlorobenzene (PhCl), ethyl acetate (AcOEt), dimethyl ether (DME), tetrahydrofuran (THF), 1,1-dichloroethane ($C_2H_4Cl_2$), 1,2-dichloroethane (DCE), pyridine, butanone, acetone, acetic anhydride ($Ac_2O$), tetramethylurea (($Me_2N)_2CO$), benzonitrile (PhCN), propionitrile ($CH_3CH_2CN$), hexamethylphosphoramide (HMPA), nitrobenzene ($PhNO_2$), nitromethane ($MeNO_2$), dimethylformamide (DMF), acetonitrile (MeCN), sulfolane, dimethylsulfoxide (DMSO), formamide ($HCONH_2$), N-methylformamide (NMF), N-methylacetamide ($CH_3CONHMe$), and acetic acid.

Preferably, according to the invention, the aprotic solvent can be dichloromethane.

According to the invention, the acetylation reaction of 12-norziza-6(13)-en-2β-ol can be carried out at a temperature between −25° C. and the solvent reflux temperature. Preferably, the reaction can be started at a temperature between −25° C. and 25° C. (13° F. to 77° F.), more preferably −25° C. and 0° C. (13° F. to 32° F.). The reaction can then progress freely until it reaches solvent reflux temperature; it can then be kept at a temperature of about 25° C. (77° F.), until all reactants are exhausted.

Those of ordinary skill in the art will readily stop the reaction when it can be observed, by sample collection and analysis, that the reaction has reached the desired stage, for example, by measuring the removal of 12-norziza-6(13)-en-2β-ol with gas chromatography or thin layer chromatography, or nuclear magnetic resonance.

The invention also relates to (2R)-12-norziza-6(13)-en-2-yl acetate, with Formula I, which can be obtained from the synthesis method, according to the invention.

The invention further relates to the use of (2R)-12-norziza-6(13)-en-2-yl acetate, as a fragrance agent. Preferably, the fragrance agent may be intended as an ingredient in any kind of composition such as perfume, eau de parfum, eau de toilette, hygiene products, cosmetics, soaps, detergents or candles.

According to the invention, (2R)-12-norziza-6(13)-en-2-yl acetate can be used alone in compositions, that is, without the (2S)-12-norziza-6(13)-en-2-yl acetate form, or in the presence of (2S)-12-norziza-6(13)-en-2-yl acetate in a weight ratio of the (2R)-12-norziza-6(13)-en-2-yl acetate form to the (2S)-12-norziza-6(13)-en-2-yl acetate form (R/S) greater than 1.2, preferably greater than 1.5.

Other invention features and advantages will emerge from the following examples, given as illustrations, but not by way of limitation, as well as from FIG. 1, which represents the gas chromatography analysis results of the synthesis reaction of (2R)-12-norziza-6(13)-en-2-yl acetate from khusimone.

Thus, FIG. 1 shows the chromatogram obtained by gas chromatography analysis of the product resulting at the end of the two steps synthesis described in Examples 1 and 2.

EXAMPLES

Example 1: Synthesis of (2R)-12-norziza-6(13)-en-2-yl acetate from khusimone

Step 1: Synthesis of 12-norziza-6(13)-en-2-ol from khusimone

In a flask, 3 mmol of khusimone are added in the presence of 6 mmol of sodium borohydride in 30 mL of ethanol to obtain a khusimone concentration 0.1M, at room temperature for 2 h. The solvent is then evaporated in vacuum and 10 mL of dichloromethane are added to the reaction mixture. Next, 10 mL of 1N hydrochloric acid are added. Following decantation, the organic phase is recovered and washed with brine, and finally dried over magnesium sulfate. After solvent evaporation, the product is obtained as a colorless oil with a 97% yield.

Step 2: synthesis of (2R)-12-norziza-6(13)-en-2-yl acetate from 12-norziza-6(13)-en-2-ol The product obtained in step 1 is mixed with acetic anhydride (2 equivalents), triethylamine (1.2 equivalents) and 4-dimethylaminopyridine (0.1 equivalents) in 10 mL of dichloromethane at room temperature for 2 h. The reaction mixture was washed with a 0.1 N hydrochloric acid solution, then with a saturated solution of sodium bicarbonate, and finally with brine. After drying over magnesium sulfate and solvent evaporation, the product is obtained as a colorless oil which crystallizes spontaneously. The reaction yield increases to 83% for (2R)-12-norziza-6(13)-en-2-yl acetate, with a purity of 98.5%.

The result of this synthesis is shown in FIG. 1, appended, wherein can be seen the chromatogram obtained by gas chromatography of the product obtained at the end of the 2 synthesis steps, shown at the top of the FIGURE.

Total removal of the starting material (khusimone) can be observed, as well as the presence of an important peak that reveals the presence of (2R)-12-norziza-6(13)-en-2-yl acetate, representing 98.5% by quantity of the total amount of (2R)- and (2S)-12-norziza-6(13)-en-2-yl acetate obtained. The presence of a minor peak can also be observed, which shows the presence of (2S)-12-norziza-6(13)-en-2-yl acetate and represents less than 1.5% by quantity of the total amount of (2R)- and (2S)-12-norziza-6(13)-en-2-yl acetate obtained.

Identification of the different compounds was made by mass spectrometry, as well as by nuclear magnetic resonance after isolation of said compounds.

The invention claimed is:
1. An isolated (3R)-epimer of octahydro-7,7-dimethyl-8-methylene-1H-3a,6-methanoazulene-3-yl acetate [(octahydro-7,7-dimethyl-8-methylene-[3R,3aR,6R,8aR]-1H-3a,6-methanoazulene-3-yl acetate) or (2R)-12-norziza-6(13)-en-2-yl acetate] of formula I

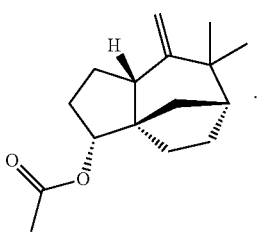

2. A composition containing a (3R)-epimer of octahydro-7,7-dimethyl-8-methylene-1H-3a,6-methanoazulene-3-yl acetate [(octahydro-7,7-dimethyl-8-methylene-[3R,3aR,6R,8aR]-1H-3a,6-methanoazulene-3-yl acetate) or (2R)-12-norziza-6(13)-en-2-yl acetate] of formula I:

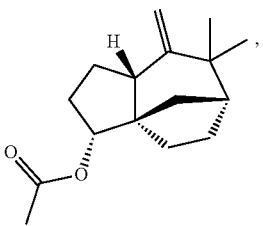

wherein (2S)-12-norziza-6(13)-en-2-yl acetate is either absent or present in an amount such that the weight ratio of (2R)-12-norziza-6(13)-en-2-yl acetate to (2S)-12-norziza-6(13)-en-2-yl acetate [(R)/(S)] is greater than 1.2.

3. The composition according to claim 2, wherein (2S)-12-norzisa-6(13)-en-2-yl acetate is absent.

4. The composition according to claim 2, wherein (2S)-12-norziza-6(13)-en-2-yl acetate is present in an amount such that the weight ratio of (2R)-12-norziza-6(13)-en-2-yl acetate to (2S)-12-norziza-6(13)-en-2-yl acetate [(R) (S)] is greater than 1.2.

5. A method for synthesizing the composition of claim 3 containing (2R)-12-norziza-6(13)-en-2-yl acetate in the absence of (2S)-12-norziza-6(13)-en-2-yl acetate, comprising:
  reducing khusimone in the presence of a reducing agent and an organic solvent to form 12-norziza-6(13)-en-2β-ol, and
  acetylating the 12-norziza-6(13)-en-2β-ol obtained in the reducing step in the presence of an organic solvent to form (2R)-12-norziza-6(13)-en-2-yl acetate.

6. The method of claim 5, wherein the reducing agent is selected from the group consisting of lithium aluminum hydride (LiAlH$_4$), DiBAH (diisobutylaluminum hydride), sodium borohydride (NaBH$_4$), lithium borohydride (NaLiH$_4$) and potassium borohydride (KBH$_4$).

7. The method of claim 5, wherein the molar ratio between the reducing agent (RA) and the khusimone (K) is between 0.5 and 5.

8. The method of claim 5, wherein the organic solvent is selected from the group consisting of methanol (MeOH), ethanol, propanol, isopropanol, n-butanol, sec-butanol, isobutanol, t-butanol, tetrahydrofuran (THF), 1,4-dioxane, dimethylsulfoxide (DMSO), acetonitrile, and mixtures in all proportions of these solvents.

9. The method of claim 5, wherein said step of acetylating 12-norziza-6(13)-en-2β-ol is carried out by reacting the 12-norziza-6(13)-en-2β-ol with an acetylating agent (Ac) in the presence of a base and a nucleophilic catalyst in an aprotic solvent.

10. The method of claim 9, wherein the acetylating agent (Ac) is selected from the group consisting of acetic anhydride, acetic acid, and acetyl chloride.

11. The method of claim 10, wherein, in said acetylating step, the molar ratio [(Ac)/(Z)] between the acetylating agent (Ac) and the 12-norziza-6(13)-en-2β-ol (Z) is between 1 and 5.

12. The method of claim 9, wherein the organic base is selected from the group consisting of N,N-diisopropylethylamine (DIPEA), triethylamine (Et$_3$N) and pyridine.

13. The method of claim 12, wherein the acetylation step is carried out with a molar ratio [(OB)/(Z)] between the organic base (OB) and the 12-norziza-6(13)-en-2β-ol (Z) of 0.1 to 5.

14. The method of claim 9, wherein the nucleophilic catalyst is selected from the group consisting of 4-(N,N-dimethylamino)pyridine (DMAP), 1,4-diazabicyclo[2.2.2]octane (DABCO), 1,8-diazabicyclo[5.4.0]undec-7-ene (DBU) and N,N'-dicyclohexylcarbodiimide (DCC).

15. The method of claim 14, wherein the step of acetylating 12-norziza-6(13)-en-2β-ol is carried out with a molar ratio [(NC)/(Z)] between the nucleophilic catalyst (NC) and the 12-norziza-6(13)-en-2β-ol (Z) of 0.01 to 10.

16. The method of claim 9, wherein the aprotic solvent is selected from the group consisting of n-hexane, cyclohexane, 1,4-dioxane, dichloromethane (DCM), carbon tetrachloride (CCl$_4$), benzene, trichloroethylene (Cl$_2$C=CHCl), tetrachloroethylene (Cl$_2$C=CCl$_2$), toluene, carbon disulfide (CS$_2$) diethyl ether (Et$_2$O), chloroform (CHCl$_3$), bromobenzene (PhBr), chlorobenzene (PhCl), ethyl acetate (AcOEt), dimethyl ether (DME), tetrahydrofuran (THF), 1,1-dichloroethane (C$_2$H$_4$Cl$_2$), 1,2-dichloroethane (DCE), pyridine, butanone, acetone, acetic anhydride (Ac$_2$O), tetramethylurea ((Me$_2$N)$_2$CO), benzonitrile (PhCN), propionitrile (CH$_3$CH$_2$CN), hexamethylphosphoramide (HMPA), nitrobenzene (PhNO$_2$), nitromethane (MeNO$_2$), dimethylformamide (DMF), acetonitrile (MeCN), sulfolane, dimethylsulfoxide (DMSO), formamide (HCONH$_2$), N-methylformamide (NMF), N-methylacetamide (CH$_3$CONHMe), and acetic acid.

17. A fragrance agent comprising (2R)-12-norziza-6(13)-en-2-yl acetate, wherein said (2R)-12-norziza-6(13)-en-2-yl acetate is present in the absence of (2S)-12-norziza-6(13) en-2-yl, or in the presence of (2S)-12-norziza-6(13)-en-2-yl, in a weight ratio of (2R)-12-norziza-6(13)-en-2-yl acetate to (2S)-12-norziza-6(13)-en-2-yl acetate (R/S) greater than 1.2.

18. In a perfume, an eau de partum, an eau de toilette, a hygiene product, a cosmetic, a soap, a detergent or a candle having a fragrance agent therein, the improvement wherein said fragrance agent comprises (2R)-12-norziza-6(13)-en-2-yl acetate.

19. The perfume, eau de partum, eau de toilette, hygiene product, cosmetic, soap, detergent or candle according to claim 18, wherein the (2R)-12-norziza-6(13)-en-2-yl acetate is present in the absence of any (2S)-12-norziza-6(13)-en-2-yl form, or is present in the presence of (2S)-12norziza-6(13)-en-2-yl, in a weight ratio of (2R)-12-norziza-6(13)-en-2-yl acetate to (2S)-12-norziza-6(13)-en-2-yl acetate (R/S) greater than 1.2.

* * * * *